United States Patent
Fried et al.

(10) Patent No.: US 11,896,838 B2
(45) Date of Patent: Feb. 13, 2024

(54) RECHARGE ALGORITHM FOR ACCURATE HEAT CONTROL ESTIMATION IN PRESENCE OF FERRITE AND ELECTRONICS

(71) Applicant: Medtronic, Inc., Minneapolis, MN (US)

(72) Inventors: Andrew Fried, Woodbury, MN (US); Brett Otteson, Minneapolis, MN (US); Douglas Brown, Shakopee, MN (US); Venkat Gaddam, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 492 days.

(21) Appl. No.: 17/078,479

(22) Filed: Oct. 23, 2020

(65) Prior Publication Data

US 2021/0121707 A1    Apr. 29, 2021

Related U.S. Application Data

(60) Provisional application No. 62/926,117, filed on Oct. 25, 2019.

(51) Int. Cl.
*A61N 1/378* (2006.01)
*H02J 50/80* (2016.01)
(Continued)

(52) U.S. Cl.
CPC ....... *A61N 1/3787* (2013.01); *A61N 1/37252* (2013.01); *H02J 50/10* (2016.02); *H02J 50/80* (2016.02)

(58) Field of Classification Search
CPC .......................... A61N 1/3787; A61N 1/37252
See application file for complete search history.

(56) References Cited

U.S. PATENT DOCUMENTS 8,509,912 B2    8/2013 Morgan et al.
8,901,778 B2    12/2014 Kesler et al.
(Continued)

FOREIGN PATENT DOCUMENTS

WO    WO 2009/134467 A1    11/2009

OTHER PUBLICATIONS

International Search Report and Written Opinion for PCT/US20/57116, dated Feb. 3, 2021, 11 pages.

*Primary Examiner* — Gary Jackson
*Assistant Examiner* — Alexander M Eisenberg
(74) *Attorney, Agent, or Firm* — Patterson Thuente IP

(57) ABSTRACT

A method for controlling charging a power source of an implantable medical device (IMD) in a patient including determining a power being delivered to a primary coil of an external charging device for recharging, determining an estimated power delivered to the IMD power source an estimated heat generated by the primary coil based on a resistance of the primary coil determined as function of at least one of a recharge frequency, a temperature of the primary coil, and a current supplied to the primary coil, calculating an estimated heat generated by the IMD by subtracting the estimated heat generated by the primary coil and the estimated power delivered stored by the rechargeable power source from the power being delivered to a primary coil; and controlling based on the heat generated by the IMD, the power being delivered by the primary coil of the external charging device.

20 Claims, 9 Drawing Sheets

(51) Int. Cl.
 *H02J 50/10* (2016.01)
 *A61N 1/372* (2006.01)

(56) References Cited

U.S. PATENT DOCUMENTS

| | | | |
|---|---|---|---|
| 9,270,134 B2 | 2/2016 | Gaddam et al. | |
| 9,653,935 B2 | 5/2017 | Cong et al. | |
| 9,789,325 B2 | 10/2017 | Shelton et al. | |
| 9,878,170 B2 * | 1/2018 | Angara | A61N 1/36071 |
| 10,226,636 B2 | 3/2019 | Gaddam et al. | |
| 10,258,804 B2 | 4/2019 | Scott et al. | |
| 10,554,069 B2 | 2/2020 | Paralikar et al. | |
| 10,666,067 B2 | 5/2020 | Higgins et al. | |
| 10,670,469 B2 | 6/2020 | Ryu et al. | |
| 2004/0257747 A1 * | 12/2004 | Stevenson | A61N 1/3754 |
| | | | 361/302 |
| 2013/0278226 A1 * | 10/2013 | Cong | H02J 7/007192 |
| | | | 320/150 |
| 2013/0289662 A1 * | 10/2013 | Olson | A61N 1/3787 |
| | | | 607/61 |
| 2018/0043167 A1 * | 2/2018 | Gaddam | A61N 1/3787 |
| 2018/0333585 A1 * | 11/2018 | Gaddam | A61N 1/3787 |
| 2019/0190296 A1 | 6/2019 | Paralikar et al. | |
| 2019/0262621 A1 | 8/2019 | Amir et al. | |
| 2019/0334367 A1 | 10/2019 | Scott et al. | |
| 2020/0001094 A1 | 1/2020 | Iyer et al. | |
| 2020/0021126 A1 | 1/2020 | Seo et al. | |
| 2020/0044458 A1 | 2/2020 | Yoon et al. | |
| 2020/0136417 A1 | 4/2020 | Paralikar et al. | |
| 2020/0136421 A1 | 4/2020 | Kim et al. | |
| 2020/0185950 A1 | 6/2020 | Jeong et al. | |
| 2020/0366133 A1 * | 11/2020 | Lee | H02J 50/12 |

\* cited by examiner

(12) United States Patent

RECHARGE ALGORITHM FOR ACCURATE HEAT CONTROL ESTIMATION IN PRESENCE OF FERRITE AND ELECTRONICS

CROSS-REFERENCE TO RELATED APPLICATIONS

This application claims the benefit of U.S. Provisional Application No. 62/926,117 filed on Oct. 25, 2019, the entirety of which is incorporated herein by reference.

FIELD

The present technology is generally related to medical devices and, more particularly, systems and methods for estimating temperatures of implantable medical devices.

BACKGROUND

Implantable medical devices (IMDs) may be used to monitor patient conditions or deliver therapy to the patient. For long term or chronic uses, IMDs may include a rechargeable power source (e.g., comprising one or more capacitors or batteries) that extends the operational life of the IMD compared to a nonrechargeable device.

Conventionally, the patient may use an external charging device to recharge the power source of the IMD when the energy stored in the rechargeable power source becomes depleted. The IMD may be charged by wireless transcutaneous charging.

In some examples, transcutaneous charging may be performed using inductive coupling between a primary coil in the charging device and a secondary coil in the IMD. When a current is applied to the primary coil (e.g., the coil in the external charging device) and the primary coil is located in close proximity to the secondary coil (e.g., the coil in the IMD), electrical current is induced in the secondary coil within the patient. Circuitry in the IMD uses the current induced in the secondary coil to charge a rechargeable power source, such as a battery, within the IMD. The external charging device does not need to physically connect (e.g., hard wired) with the rechargeable power source for charging to occur.

SUMMARY

The disclosure describes systems and techniques for estimating the heat generation or temperature of a portion of an implantable medical device (IMD) without the need for a temperature sensor within the IMD. For example, the disclosed systems may use a described algorithm to accurately estimate energy transfer and loss within the recharging system to estimate the heat generated by or the tissue contacting surface temperature of an IMD to maintain the IMD, external charger, or both below a threshold operating value. The IMD may include a rechargeable power source that can be transcutaneously charged. During the charging session, the process of inductive coupling may generate heat within the IMD and charger by electrical current flowing within electrical components within the IMD and charger as part of the charging process. Other sources of heat generation, such as eddy currents generated in the external case forming a housing of the IMD, or increased surrounding tissue temperature from direct tissue heating, may also increase the temperature of various components of the IMD as a byproduct of the charging process. In order to both maximize the amount of power delivered to the IMD while also minimizing the duration of the recharging process and maintain the IMD below a threshold temperature, it becomes important to accurately determine the heat generation or temperature of both the IMD and charger so maintain the recharging system within desired temperature conditions. The IMD or the external charger may monitor or control the temperature of the IMD through regulation of the power levels or the duration of the charging session to maintain a target temperature or temperature range during the charging process.

The devices, systems, and techniques described herein allow for the estimation of the heat generation or temperature of an IMD during a recharging process even when the IMD does not include a temperature sensor as part of its construction. Thus, the heat generation or temperature of the IMD must be estimated using a conservation of energy analysis on the system as a whole. By controlling the charging of the IMD based on the estimated heat generation or temperature of the IMD, the IMD or external charger may provide faster recharge sessions while also maintaining safe operating temperatures of the IMD for the patient.

In one aspect, the present disclosure provides a method for controlling charging of a rechargeable power source of an implantable medical device (IMD) in a patient. The method includes, by processing circuitry, determining a power being delivered to a primary coil of an external charging device for recharging the IMD; determining an estimated power delivered stored by the rechargeable power source during charging of the IMD; calculating an estimated heat generated by the primary coil based on a resistance of the primary coil, wherein the resistance of the primary coil is determined as function of at least one of a recharge frequency, a temperature of the primary coil, and a current supplied to the primary coil; calculating, by the processing circuitry, an estimated heat generated by the IMD by subtracting the estimated heat generated by the primary coil and the estimated power delivered to the rechargeable power source from the power being delivered to a primary coil; and controlling, based on the heat generated by the IMD, the power being delivered by the primary coil of the external charging device.

In one aspect, the present disclosure provides an external charging device including a primary coil configured to provide recharge power to a rechargeable power source of an implantable medical device (IMD) through transcutaneous charging, a ferrite material adjacent to the primary coil and spanning an aperture defined by the primary coil, and processing circuitry configured to determine a power being delivered to the primary coil of the external charging device for recharging the IMD; determine an estimated power delivered stored by the rechargeable power source during charging of the IMD; calculate an estimated heat generated by the primary coil based on a resistance of the primary coil, where the resistance of the primary coil is determined as function of at least one of a recharge frequency, a temperature of the primary coil, and a current supplied to the primary coil; calculate an estimated heat generated by the IMD by subtracting the estimated heat generated by the primary coil and the estimated power delivered stored by the rechargeable power source from the power being delivered to the primary coil; and control, based on the heat generated by the IMD, the power being delivered by the primary coil of the external charging device.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
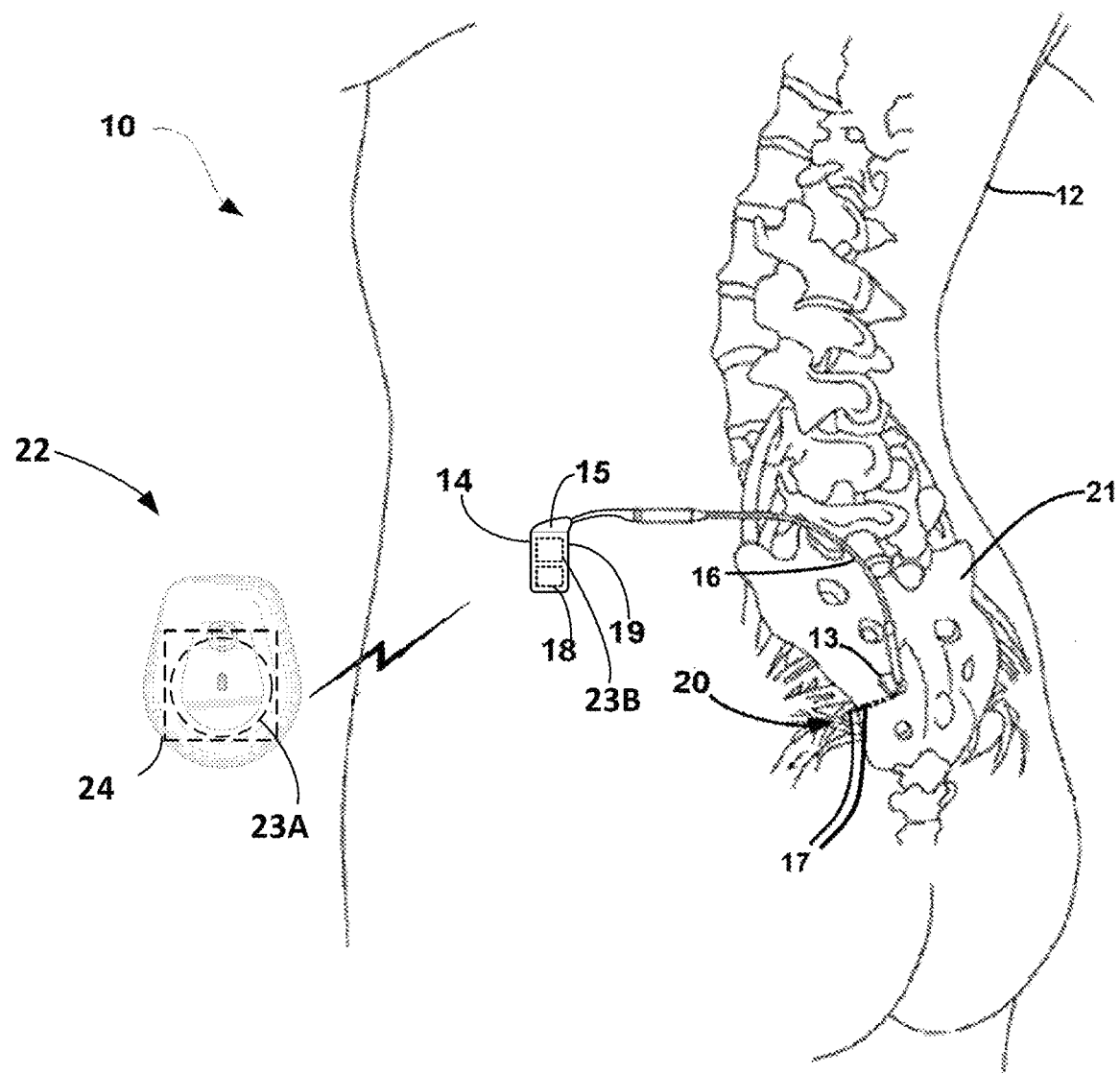
FIG. 1 is a conceptual diagram illustrating an example system that includes an implantable medical device (IMD) and an external charging device that charges a rechargeable power source of the IMD in accordance with the techniques described in this disclosure.

The disclosure describes systems and techniques for estimating the heat generated by or the external temperature of an IMD without the need for a temperature sensor to be included in the construction of the IMD. For example, a system may monitor and control various charging parameters of the recharger system including, for example, the charging power of the external charger, the current of the external charger, the frequency of recharge, and the like, associated with charging a rechargeable power source of an IMD and control one or more of these parameters during the charging session to maintain the system within desired operational thresholds.

IMDs may be implanted within a patient and perform one or more tasks, such as monitoring a parameter of the patient or delivering a therapy to the patient. To extend the operational life of the IMD, the IMD may include a rechargeable power source (e.g., one or more capacitors or batteries). During recharge, the power transmitted to the IMD may generate heat that increases the temperature of the IMD during the recharging session. The heat generation may be due to resistance within the circuitry of the IMD, inefficiencies with the coupling between the recharging circuitry of the IMD and the charging circuitry of the external charging device providing the power to recharge the IMD, and the like. Additional heat may be generated in the housing of the IMD due to eddy currents caused by the varying magnetic fields present during the charging session or from current flowing from the secondary coil of the IMD to the battery or other sources. Elevated temperatures within the IMD may be undesirable and could cause discomfort to the patient.

Providing an accurate estimation of the heat generated by or the external temperature of an IMD may allow the system to be more efficient during the recharge session by transferring power from the charging device to the IMD at a higher rate for a longer period of time while the temperature of the IMD is within desirable parameters. Generally, increasing the recharge rate, while decreasing the duration of recharge, may result in a faster increase in the IMD temperature (e.g., the internal and external portions of the IMD) as compared to lower charging rates. However, because the IMD is implanted within the patient, it can be challenging to determine an accurate reading of the temperature of the device, in particular the surface temperature of the IMD in contact with the patient which may be different than the hottest part of the IMD or where the thermal sensor is located. In some embodiments, IMDs exclude internal temperature sensors or other electronics to make the devices smaller and lower power. Thus, the surface temperature of the IMD may be unknown during the recharge session and the recharger algorithm may estimate the IMD temperature based on recharge parameters. Overestimating the temperature of the IMD may lead to premature reduction of recharging rates to ensure that the external temperature of the IMD remains within predefined safety or patient comfort limits. In other embodiments, the IMD may include one or more temperature sensors, which may be used as safeguard or to assess the accuracy of the disclosed algorithm.

As the recharging systems become more sophisticated in order to optimize recharging, the systems may become more and more sensitive to fluctuations in temperatures. For example, as discussed further below, one problem faced with recharging an IMD is the misalignment between the primary coil of the external charger and the secondary coil of the IMD. IMDs may be placed in locations such as the lower back of a patient which can be challenging for a patient to physically reach, much less place and properly align an external recharger. One technique for decreasing inefficiencies associated with improper alignment between the primary and secondary coils is to include a ferrite core within the external charger adjacent to the primary coil which can help redirect or focus the magnetic field lines generated by the primary coil towards the secondary coil causing the system to be less susceptible to misalignment between the coils. Additionally, or alternatively, the ferrite material may also help shield sensitive electronic components of the recharging device during the recharge session.

It has been observed that the inclusion of a ferrite material within the external charger can alter the resistance and heat generation within the external charger particularly as the recharge frequency, current, and temperature of the external charger is altered. Accurately accounting for such changes can be used to provide a more accurate assessment of the energy conservation in the system and optimize the recharge session.

FIG. 1 is a conceptual diagram illustrating an example recharge system 10 that includes an implantable medical device (IMD) 14 that charges a rechargeable power source 18 of IMD 14 in accordance with the techniques described in this disclosure, and an external charging device 22. Although the techniques described in this disclosure are generally applicable to a variety of medical devices including medical devices such as patient monitors, electrical stimulators, or drug delivery devices, application of such techniques to implantable electrical stimulators (e.g., neurostimulators) will be described for purposes of illustration.

As shown in FIG. 1, system 10 includes an IMD 14 and external charging device 22 shown in conjunction with a patient 12 (e.g., human). In the embodiment of FIG. 1, IMD 14 is an implantable electrical stimulator that delivers neurostimulation therapy to patient 12, e.g., for relief of chronic pain or other symptoms. Generally, IMD 14 may be a chronic electrical stimulator that remains implanted within patient 12 for an extended period of time (e.g., months or years). IMD 14 may be implanted in a subcutaneous tissue pocket, within one or more layers of muscle or fat, or other internal location of patient 12. IMD 14 and lead 16 may be directed for sacral nerve stimulation (SNS) therapy, pudendal nerve stimulation therapy, pelvic floor disorders or treating other disorders.

IMD 14 includes rechargeable power source 18, such as a rechargeable battery. IMD 14 may be coupled physically or electrically to lead 16 by connector block 15. IMD 14 may include a housing 19 that may contact tissue of patient 12 in the area adjacent to the implant site of IMD 14. As used in this disclosure, housing 19 may comprise a housing or other structure that provide one or more external portions of IMD 14, excluding lead 16, which may be brought into direct contact with tissue of patient 12 when implanted. In general, the external temperature of IMD 14 may refer to the temperature of housing 19 or a portion thereof.

In the embodiment of FIG. 1, lead 16 is disposed within patient 12, e.g., implanted within patient 12 proximate to a target tissue site 20. Target tissue site 20 may be a site proximate of the S3 sacral nerve of patient 12. In this example, in order to implant distal end of lead 16 proximate to the S3 sacral nerve, lead 16 may be introduced into the S3 sacral foramen 13 of sacrum 21 to access the S3 sacral nerve. For some patients, stimulation of the S3 sacral nerve may be effective in treating a pelvic floor disorder of the patient.

Although lead 16 may be a single lead, lead 16 may include a lead extension or other segments that may aid in implantation or positioning of lead 16. In addition, a proximal end of lead 16 may include a connector block 15 that electrically couples to a header of IMD 14. In various examples, connector block 15 may be considered part of the housing 19 or an external surface of IMD 14. Additionally, or alternatively system 10 may include two or more leads, each coupled to IMD 14 and directed to similar or different target tissue sites.

Although FIG. 1 illustrates placement of lead 16 proximate to the S3 sacral nerve for delivery of stimulation to the S3 sacral nerve, in other embodiments, delivery of stimulation to the pudendal nerve of patient 12 may more specifically target the pelvic floor muscles of patient 12. For example, in some examples, stimulation of the S3 sacral nerve (e.g., sacral nerve stimulation or SNS) may activate one or more leg muscles of patient 12, in addition to activating one or more pelvic floor muscles. Activation of the one or more leg muscles may be unnecessary and unwanted in treatment for strengthening the pelvic floor muscles of patient 12. In some examples, stimulation of the pudendal nerve can more specifically target pelvic floor muscles, e.g., the external urethral sphincter, without activation of the one or more leg muscles. SNS may be used to treat patients suffering from any number of pelvic floor disorders such as pain, urinary incontinence, fecal incontinence, sexual dysfunction, or other disorders treatable by targeting one or more sacral nerves. Additionally, while IMD 14 is discussed in the context of treating pelvic disorders, the techniques and algorithms regarding recharging of IMD 14 disclosed herein may be applicable to other types of IMDs used for treating other types of disorders. For example, lead 16 may be configured to provide deep brain stimulation (DBS), peripheral nerve stimulation (PNS), gastric stimulation to treat obesity or gastroparesis, tibial nerve stimulation, or other deep tissue or more superficial types of electrical stimulation. In other embodiments, lead 16 may provide one or more sensors configured to allow IMD 14 to monitor one or more parameters of patient 12. The one or more sensors may be provided in addition to, or in place of, therapy delivery by lead 16. Examples of additional stimulation therapy systems and stimulation parameters can be found in for example, U.S. Pat. No. 10,201,702 B2 by Bonde et al., U.S. Pat. No. 8,467,875 B2 by Bennett et al., and U.S. Pat. No. 9,446,235 B2 by Su et al., each of which is incorporated by reference in its entirety.

Lead 16 may carry one or more electrodes 17 that are placed adjacent to the target tissue site 20, e.g., adjacent the S3 sacral nerve. One or more electrodes 17 may be disposed at a distal tip of lead 16 or at other positions at intermediate points along lead 16, for example. Electrodes 17 of lead 16 transfer electrical stimulation generated by an electrical stimulation generator in IMD 14 to tissue site 20 of patient 12. Electrodes 17 of lead 16 may be ring electrodes, segmented electrodes, or partial ring electrodes. Segmented electrodes may be useful for targeting different fibers of the same or different nerves to generate different physiological effects or for delivering relatively high frequency stimulation (e.g., about 66 Hertz) and relatively low frequency stimulation (e.g., about 15 Hertz) to activate both fast twitch muscles and slow twitch muscles substantially simultaneously or at alternating time slots. In some cases, delivering stimulation via one or more electrodes and/or segmented electrodes may help achieve a more uniform electrical field or activation field distribution relative to the nerve in some examples, which may help minimize discomfort to patient 12 that results from the delivery of electrical stimulation.

Although lead 16 is described as generally delivering or transmitting electrical stimulation signals, lead 16 may additionally or alternatively transmit electrical signals sensed from patient 12 to IMD 14 for monitoring. For example, IMD 14 may utilize detected nerve impulses to diagnose the condition of patient 12 or to adjust the delivered stimulation therapy. Lead 16 may thus transmit electrical signals to and from patient 12.

IMD 14 may be constructed of any polymer, metal, ceramic, or composite material sufficient to house the components of IMD 14 (e.g., components illustrated in FIG. 2) within patient 12. In some such embodiments, IMD 14 may be constructed with a biocompatible housing, such as titanium or stainless steel, or a polymeric material such as silicone, polysulfone, or polyurethane, and surgically implanted at a site in patient 12 near the pelvis, abdomen, or buttocks. The housing 19 of IMD 14 may be configured to provide a hermetic seal for components including rechargeable power source 18. In addition, the housing of IMD 14 may be selected of a material that facilitates receiving energy to charge rechargeable power source 18.

Figure 2:
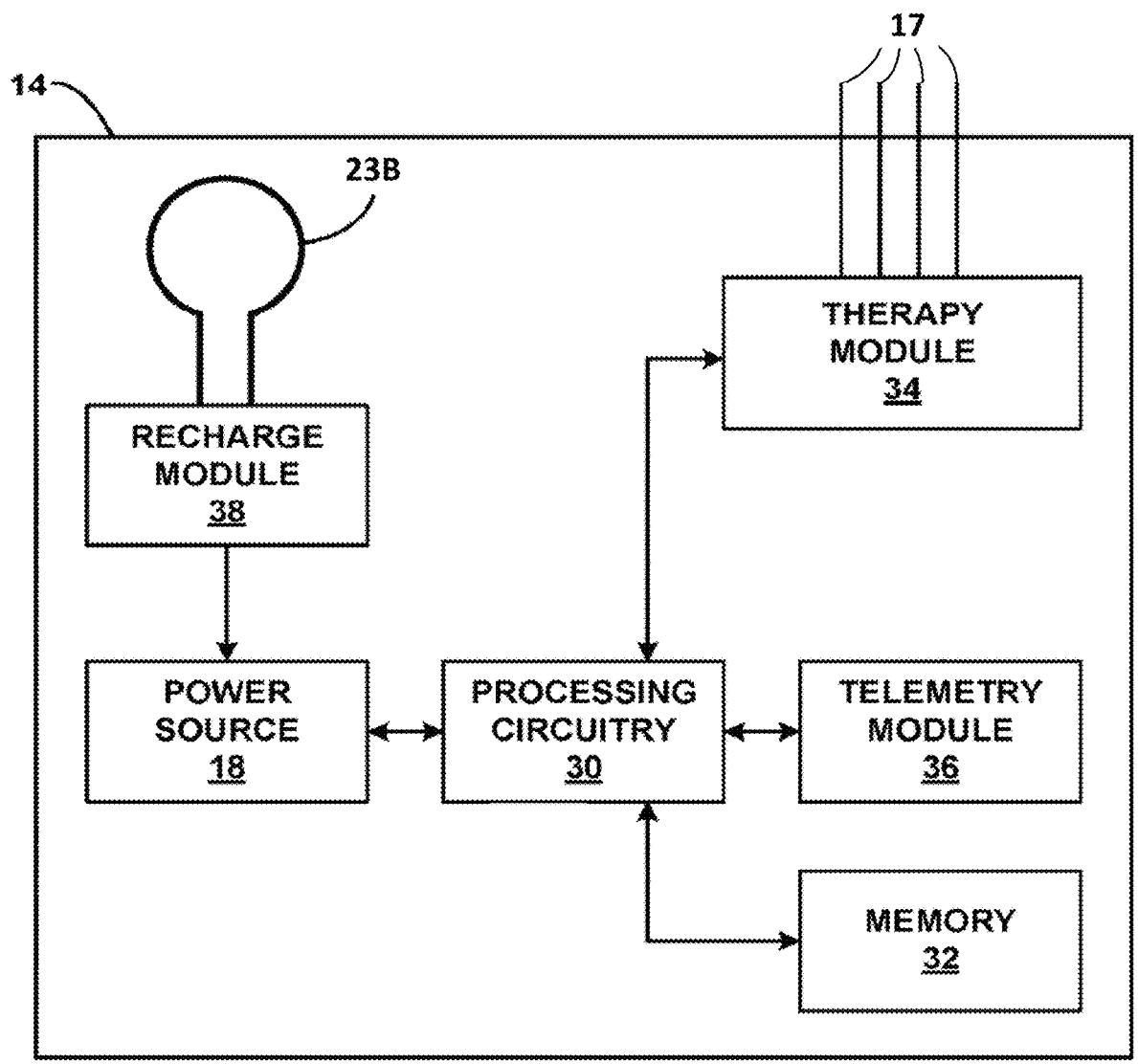
FIG. 2 is a block diagram of the example IMD of FIG. 1.

FIG. 2 is a block diagram illustrating example components of IMD 14 of FIG. 1. As shown in FIG. 2, IMD 14 includes rechargeable power source 18, secondary coil 23B, processing circuitry 30, therapy module 34, recharge module 38, memory 32, and telemetry module 36. In general, IMD 14 may comprise any suitable arrangement of hardware, alone or in combination with software or firmware, to perform the various techniques described herein attributed to IMD 14 and processing circuitry 30, and any equivalents thereof. Thus, in other embodiments, IMD 14 may include a greater or a fewer number of components.

IMD 14 includes components to receive power from external charging device 22 to recharge rechargeable power source 18 when rechargeable power source 18 has been at least partially depleted. As shown in FIG. 2, IMD 14 includes rechargeable power source 18, secondary coil 23B, and recharge module 38 coupled together. Recharge module 38 may include any of a variety of charging or control circuitries configured to process or convert current induced in secondary coil 23B into charging current to charge power source 18. Although processing circuitry 30 may provide some commands to recharge module 38, in some examples, processing circuitry 30 may not need to control any aspect of recharging and such aspects may be controlled by the processing circuitry of external charging device 22.

Secondary coil 23B may include a coil of wire or other device capable of inductive coupling with primary coil 23A disposed external to patient 12. Although secondary coil 23B is illustrated schematically as a simple loop in FIGS. 1 and 2, secondary coil 23B may include multiple turns of conductive wire. Secondary coil 23B may include a winding of wire configured such that an electrical current can be induced within secondary coil 23B from a magnetic field. The induced electrical current may then be used to recharge rechargeable power source 18. In this manner, the electrical current may be induced in secondary coil 23B associated with rechargeable power source 18. The induction may be caused by electrical current generated in the primary coil of external charging device 22, where the level of the current may be based on the selected power level. The coupling between secondary coil 23B and primary coil 23A of external charging device 22 may be dependent upon the alignment of the two coils. Generally, the coupling efficiency increases when the two coils share a common axis and are in close proximity to each other.

Recharge module 38 may include one or more circuits that process, filter, convert or transform the electrical signal induced in secondary coil 23B to an electrical signal capable of recharging rechargeable power source 18. For example, in alternating current induction, recharge module 38 may include a half-wave rectifier circuit or a full-wave rectifier circuit configured to convert alternating current from the induction to a direct current for rechargeable power source 18. The full-wave rectifier circuit may be more efficient at converting the induced energy for rechargeable power source 18 when the incident field strength is high. However, a half-wave rectifier circuit may be used to convert energy to the rechargeable power source 18 at a higher efficiency when the incident field strength is lower. In some embodiments, recharge module 38 may include both a full-wave rectifier circuit and a half-wave rectifier circuit such that recharge module 38 may switch between each circuit to control the charging rate of rechargeable power source 18.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable such that source 18 can be replenished, refilled, or otherwise capable of increasing the amount of energy stored within the device after energy has been depleted from rechargeable power source 18. Rechargeable power source 18 may also be configured to provide operational power to IMD 14 during the recharge process. In some embodiments, rechargeable power source 18 may be subjected to numerous discharge and charge cycles (e.g., hundreds or even thousands of cycles) over the operational life of rechargeable power source 18 and IMD 14.

Although rechargeable power source 18, recharge module 38, and secondary coil 23B are shown as contained within the housing of IMD 14, in alternative implementations, one or more of these components may be disposed outside of housing 19. For example, in some implementations, secondary coil 23B may be disposed outside of housing 19 of IMD 14, but still interior to the patient 12, to facilitate better coupling between secondary coil 23B and the primary coil of external charging device 22. In any case, rechargeable power source 18 may provide operational electrical power to one or more components of IMD 14.

Processing circuitry 30 of IMD 14 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the processing circuitry 30 to perform the actions attributed to this circuitry. Moreover, although processing circuitry 30, therapy module 34, recharge module 38, and telemetry module 36 are described as separate modules. In some embodiments, some combination of processing circuitry 30, therapy module 34, recharge module 38, and telemetry module 36 are functionally integrated. In some embodiments, processing circuitry 30, therapy module 34, recharge module 38, and telemetry module 36, correspond to individual hardware units, such as ASICs, DSPs, FPGAs, or other hardware units.

Memory 32 may store therapy programs or other instructions that specify therapy parameter values for the therapy provided by therapy module 34 and IMD 14. In some examples, memory 32 may also store instructions for recharging rechargeable power source 18, instructions for communication between IMD 14 and external charging device 22, or any other instructions required to perform tasks attributed to IMD 14.

Therapy module 34 may generate and deliver electrical stimulation under the control of processing circuitry 30. For example, therapy module 34 may be configured to generate and deliver electrical stimulation therapy via one or more of electrodes 17 using an appropriate therapy regimen know to those in the art. For example, during use, therapy module 34 may execute programming to deliver electrical stimulation energy, which may be constant current or constant voltage-based pulses, to one or more targeted locations within patient 12 via one or more electrodes 17 of lead 16. The parameters for a program that controls delivery of stimulation energy by IMD 14 may include information identifying which electrodes 17 have been selected for delivery of stimulation according to a stimulation program, the polarities of the selected electrodes, e.g., the electrode configuration for the program, and voltage or current amplitude, pulse rate, pulse shape, and pulse width of stimulation delivered by the electrodes 17. Electrical stimulation may be delivered in the form of stimulation pulses or continuous waveforms, for example.

In some embodiments, processing circuitry 30 may transmit additional information to external charging device 22 related to the operation of rechargeable power source 18. For example, processing circuitry 30 may use telemetry module 36 and an antenna (e.g., separate antenna or, in some embodiments, secondary coil 23B) to transmit indications that rechargeable power source 18 is completely charged, rechargeable power source 18 is fully discharged, or any other charge status of rechargeable power source 18. In some embodiments, processing circuitry 30 may use telemetry module 36 to transmit instructions to external charging device 22, including, for example, instructions to lower the power level or to terminate the charging session based on the estimated temperature of the housing 19 of IMD 14 or information that indicates any problems or errors with rechargeable power source 18 that may prevent rechargeable power source 18 from providing operational power to the components of IMD 14. In various examples, processing circuitry 30 may receive, through telemetry module 36, instructions for algorithms, including formulas or values for constants or variables to be used in the formulas that may be used to determine the temperature of the housing 19.

Figure 3:
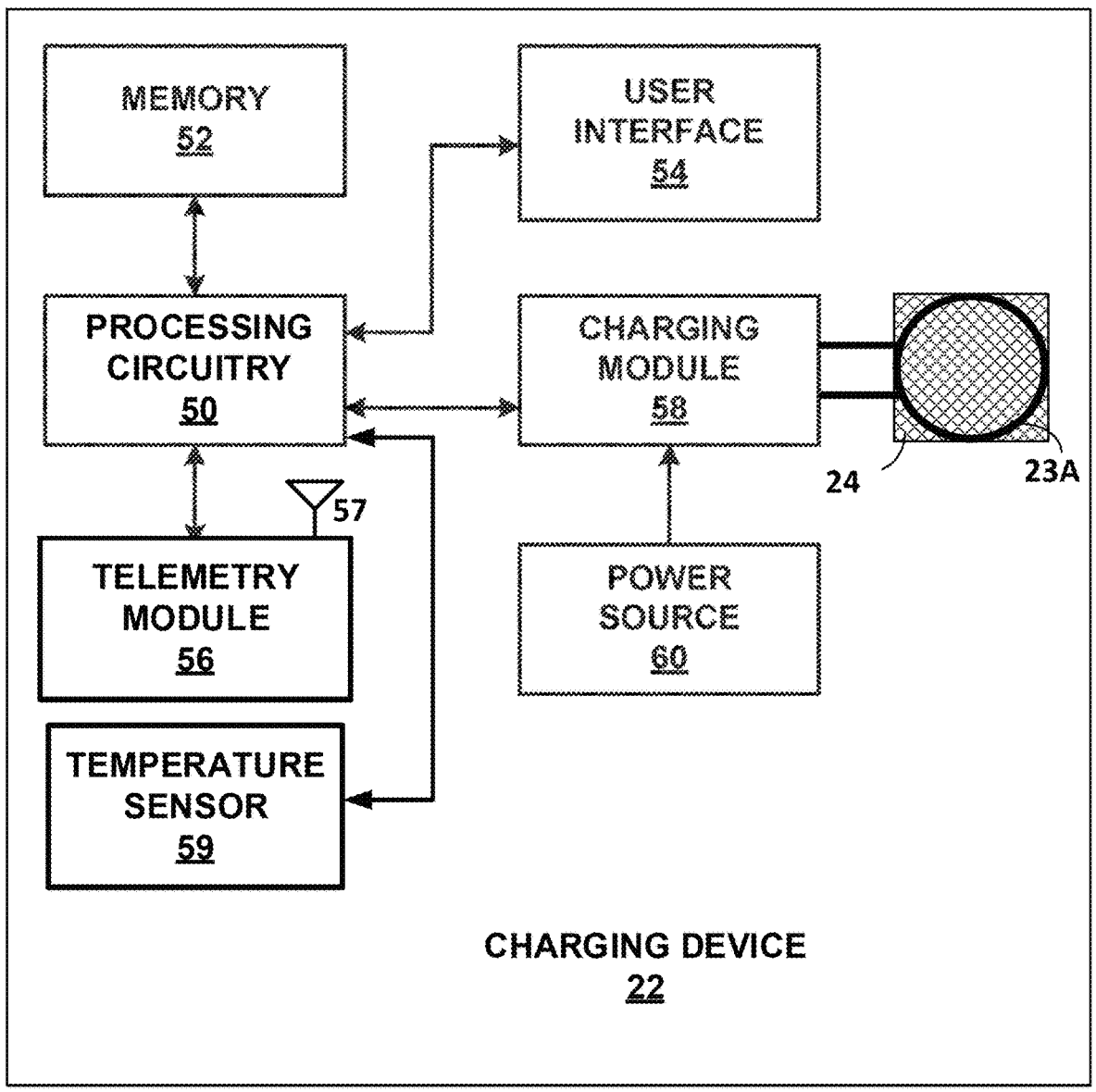
FIG. 3 is a block diagram of the example charging device of FIG. 1.

System 10 also includes external charging device 22 used to recharge rechargeable power source 18 of IMD 14 implanted in patient 12. FIG. 3 is a block diagram of the example external charging device 22. While charging device 22 may generally be described as a hand-held device, charging device 22 may be a larger portable device or a more stationary device and may be configured to communicate with an external programmer. As illustrated in FIG. 3, charging device 22 may include primary coil 23A, ferrite material 24, processing circuitry 50, memory 52, user interface 54, telemetry module 56, charging module 58, temperature sensor 59, and power source 60. Memory 52 may store instructions that, when executed by processing circuitry 50, cause processing circuitry 50 and external charging device 22 to provide the functionality ascribed to external charging device 22 throughout this disclosure.

In general, charging device 22 comprises any suitable arrangement of hardware, alone or in combination with software and/or firmware, to perform the techniques attributed to charging device 22, and processing circuitry 50, user interface 54, telemetry module 56, and charging module 58 of charging device 22. In various examples, charging device 22 may include one or more processors, such as one or more microprocessors, DSPs, ASICs, FPGAs, or any other equivalent integrated or discrete logic circuitry, as well as any combinations of such components. Charging device 22 also, in various examples, may include a memory 52, such as RAM, ROM, PROM, EPROM, EEPROM, flash memory, or a hard disk, comprising executable instructions for causing the one or more processors to perform the actions attributed to them. Moreover, although processing circuitry 50 and telemetry module 56 are described as separate modules, in some examples, processing circuitry 50 and telemetry module 56 are functionally integrated. In some examples, processing circuitry 50 and telemetry module 56 and charging module 58 correspond to individual hardware units, such as ASICs, DSPs, FPGAs, or other hardware units.

Memory 52 may store instructions that, when executed by processing circuitry 50, cause processing circuitry 50 and charging device 22 to provide the functionality ascribed to charging device 22 throughout this disclosure. For example, memory 52 may include instructions that cause processing circuitry 50 to calculate estimated energy transfers, establish thresholds, select power levels based on the estimated energy transfers and otherwise control charging module 58, communicate with IMD 14, or instructions for any other functionality. In addition, memory 52 may include a record of selected power levels, user selectable recharged modes (e.g., heat control settings, max temperature, session time, or the like), calculated estimated energy transfers, or any other data related to charging rechargeable power source 18. Processing circuitry 50 may, when requested, transmit any of this stored data in memory 52 to another computing device for review or further processing.

In some examples, memory 52 may be configured to store data representative of parts of the energy conservation equation used by processing circuitry 50 to determine heat generated by charging device 22 or IMD 14 at a particular charging frequency. In some examples, memory 52 may be configured to store data representative of a tissue model used by processing circuitry 50 to calculate tissue temperature based on tissue model and power transmitted to rechargeable power source 18 over a period of time. Tissue model may indicate how temperate of tissue surrounding IMD 14 changes over time based on, i.e., as a function of, the estimated energy transfer. Therefore, processing circuitry 50 may be able to estimate tissue temperature without direct measurement of the temperature of tissue surrounding the housing of IMD 14.

Optional user interface 54 may include a button or keypad, lights, a speaker for voice commands, a display, such as a liquid crystal (LCD), light-emitting diode (LED), or the like. In some examples the display may be a touch screen. As discussed in this disclosure, processing circuitry 50 may present and receive information relating to the charging of rechargeable power source 18 via user interface 54. For example, user interface 54 may indicate when charging is occurring, quality of the alignment between coils 23A and 23B, the selected power level, current charge level of rechargeable power source 18, duration of the current recharge session, anticipated remaining time of the charging session, or any other information. Processing circuitry 50 may receive some of the information displayed on user interface 54 from IMD 14 in some examples.

Charging device 22 also includes components to transmit power to recharge rechargeable power source 18 associated with IMD 14. As shown in FIG. 3, charging device 22 includes primary coil 23A and charging module 58 coupled to power source 60. Charging module 58 may be configured to generate an electrical current in primary coil 23A from voltage stored in power source 60. Charging module 58 may generate the electrical current according to a power level selected by processing circuitry 50 based on the estimated energy transfer. As described herein, processing circuitry 50 may select a high-power level, low power level, or a variety of different power levels to control the rate of recharge in rechargeable power source 18 and the heat generated by or the temperature of IMD 14.

Primary coil 23A may include a coil of wire, e.g., having multiple turns, or other device capable of inductive coupling with a secondary coil 23B disposed within patient 12. Primary coil 23A may include a winding of wire configured such that an electrical current generated within primary coil 23A can produce a magnetic field configured to induce an electrical current within secondary coil 23B.

Charging device 22 also includes a ferrite material 24 positioned adjacent to primary coil 23A. In some embodiments, ferrite material 24 may be in the form of a plane that spans across the aperture defined by primary coil 23A such that primary coil 23A is positioned between ferrite material 24 and secondary coil 23B during the recharge process. Primary coil 23A may be constructed of certain dimensions and/or driven to produce electromagnetic energy of a particular recharge frequency, power, and current selected for secondary coil 23B. Ferrite material 24 may help redirect or focus the magnetic field lines generated by primary coil 23A towards secondary coil 23B, thereby increasing the efficiency of the recharge process. In this manner, the electrical current may be induced in secondary coil 23B associated with rechargeable power source 18. The induced electrical current may then be used to recharge rechargeable power source 18. While the coupling efficiency between secondary coil 23B and primary coil 23A of charging device 22 may be dependent upon the alignment of the two coils, the presence of ferrite material 24 may help diminish such effects on the recharge efficiency of system 10.

Charging module 58 may include one or more circuits that generate an electrical signal, and an electrical current, within primary coil 23A. Charging module 58 may generate an alternating current of specified amplitude and frequency to transmit various levels of power to IMD 14. In this manner charging module 58 may be configured to charge rechargeable power source 18 of IMD 14 with the selected power level. The power level that charging module 58 selects for charging may be used to vary one or more parameters of the electrical signal generated for secondary coil 23B. For example, the selected power level may specify a wattage, electrical current of primary coil 23A, current amplitude, voltage amplitude, pulse rate, pulse width, or any other parameter that may be used to modulate the power transmitted by primary coil 23A. In this manner, each power level may include a specific parameter set that specifies the signal for each power level. Changing from one power level to another power level, e.g., a high-power level to a low power level, may include adjusting one or more parameters. The parameters of each power level may be selected based on hardware characteristics of charging device 22, IMD 14, or both as well as the other considerations discussed herein.

Charging device 22 also includes one or more temperature sensors 59. These temperature sensors 59 are not limited to any particular type of temperature sensor and may include one or a combination of temperature sensors such as a thermistor, a thermocouple, or a resistance thermometer, that are arranged to sense a temperature of some portion of charging device 22 (e.g., temperature of primary coil 23A). As discussed further below, the one or more of temperature sensors 59 may be used to monitor the temperature of charging device 22 to provide a more accurate assessment of the energy conservation in the recharge cycle and optimize the recharge process. Temperatures may be sampled at a rate necessary to effectively control the charging session, but the sampling rate may be reduced to conserve power as appropriate. In some embodiments, the temperature may be sampled at different rates, e.g., on the order of microseconds, milliseconds, seconds, minutes, or the like.

Power source 60 may deliver operating power to the components of charging device 22. Power source 60 may also deliver the operating power to drive primary coil 23A during the charging process. Power source 60 may include a battery and a power generation circuit to produce the operating power. In some examples, the battery may be rechargeable to allow extended portable operation. In other examples, power source 60 may draw power from a wired voltage source such as a consumer or commercial power outlet.

Telemetry module 56 may include an antenna 57, which may take on a variety of forms, such as an internal or external antenna. Telemetry module 56 supports wireless communication between IMD 14 and charging device 22 under the control of processing circuitry 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

To estimate the heat generated by IMD 14 during recharging of power source 18, an energy balance approach may be used to evaluate the energy transfer and loss in system 10. For example, the estimated energy transfer to the patient 12 may be determined by determining the total power delivered to primary coil 23A and subtracting the electrical heat generated in primary coil 23A and total power 64 delivered to the battery of IMD 14. In some examples, the estimated energy balance may be represented as Equation 1:

$$Q_{IMD} = P_{CHARGER} - Q_{CHARGER} - P_{IMD} \tag{1}$$

where all values are in Watts (W) and:

$Q_{IMD}$ is the electrical heat generated within IMD 14 caused by the resistance ($R_{IMD}$) in one or more circuits between secondary coil 23B and power source 18;

$P_{CHARGER}$ is the electrical power generated by external charger 22 and delivered through primary coil 23A as part of the recharge process. The $P_{CHARGER}$ may be considered separate from other power being used within external charger 22 that may likewise cause electrical heat generated within external charger 22 separate from the loss occurring in the recharge circuit. Such other power usage may include, for example, power used to run and operate user interface 54, telemetry module 56, temperature sensor 59, or other components of external charger 22. These other uses of power, and associated power losses are typically independent of the recharge process and do not directly influence the heating effect within IMD 14 during the recharge process.

$Q_{CHARGER}$ is the electrical heat generated by the internal resistance ($R_{PRIM}$) in charging device 22 through primary coil 23A as part of the recharging circuit; and $P_{IMD}$ is the useful recharge power delivered to IMD 14 and used to replenish power source 18.

In some embodiments, $Q_{CHARGER}$ may be measured according to Equation 2:

$$Q_{CHARGER} = R_{PRIM} * (I_{CHARGER})^2 \tag{2}$$

where $R_{PRIM}$ is the internal resistance (ohms) of charging device 22 through primary coil 23A and $I_{CHARGER}$ is the current passing through primary coil 23A during the recharge cycle which is on the order of 0.4 Amps.

The above equations may be successfully implemented to assess the energy conservation in some recharger systems that do not include the presence of a ferrite material 24 within external charger 22. Example algorithms discussing how to quantify components of Equations 1 and 2 as well as other potential contributions to the energy conservation equation are discussed in, for example, U.S. Pat. No. 9,270,134 B2 to Gaddam et al., U.S. Pat. No. 10,226,636 B2 to Gaddam et al., and U.S. Patent Application Publication No. 2019/0190296 to Paralikar et al., each of which is incorporated by reference in its entirety.

In some embodiments, $P_{CHARGER}$ may be determined by real-time measurement of coil current and applied voltage by the charging module. $P_{IMD}$ may be determined by measurement of voltage and current supplied to rechargeable power source 18 and which may, for example, be transmitted from IMD 14 to charging device 22 via telemetry module 36.

Figure 4:
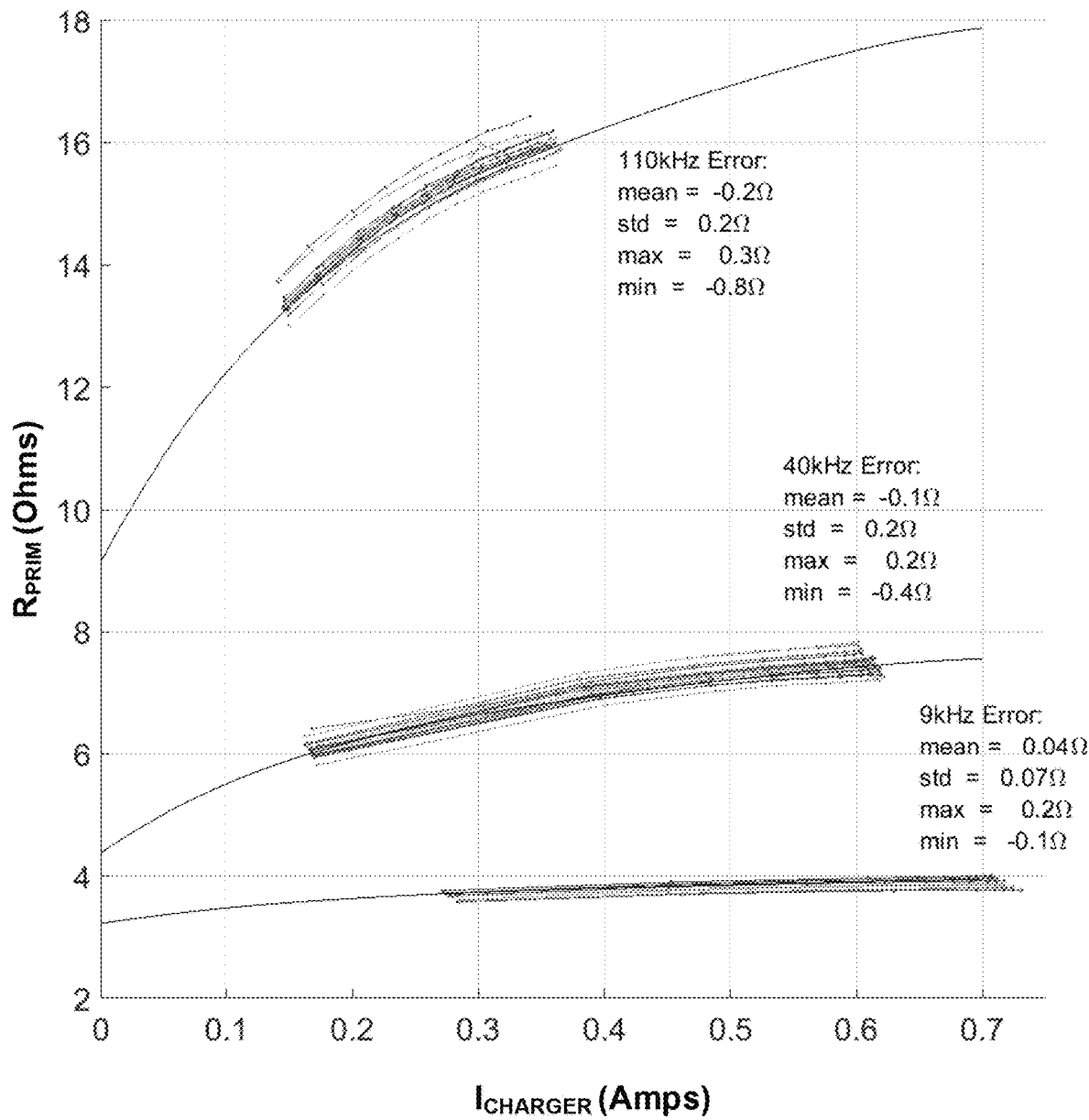
FIG. 4 is a graph of example resistance within the primary coil of the external charger for various recharging frequencies as a function of recharge current at room temperature.

The inclusion of ferrite material 24 within external charger 22 introduces unanticipated complications when assessing the energy conservation during the recharging process, particularly when recharge is performed at higher recharge frequencies (e.g., greater than 40 kHz). In part due to magnetic hysteresis effects, the inclusion of ferrite material 24 greatly influences the observed resistance through primary coil 23A making $R_{PRIM}$ and $Q_{CHARGER}$ dependent on the recharge frequency, temperature, and current of primary coil 23A during the recharge process. For example, FIG. 4 is a graph of example data collected for an external charger device (e.g., charger device 22) for a variety of recharge currents and recharge frequencies. As can be seen from FIG. 4 during operational recharge at relatively low recharge frequencies (e.g., approximately 9 kHz) $R_{PRIM}$ remains relatively constant for a variety or recharging currents (e.g., between about 0.15 Amps to about 0.7 Amps). Thus, assuming a constant $R_{PRIM}$ in these situations provided a relatively accurate assessment for $Q_{CHARGHER}$. However, as the recharge frequency is increased (e.g., increased toward about 110 kHz), $R_{PRIM}$ began to both discernibly increase with increasing recharge frequency as well as increase with increasing recharge current ($I_{CHARGER}$) and temperature.

Figure 5:
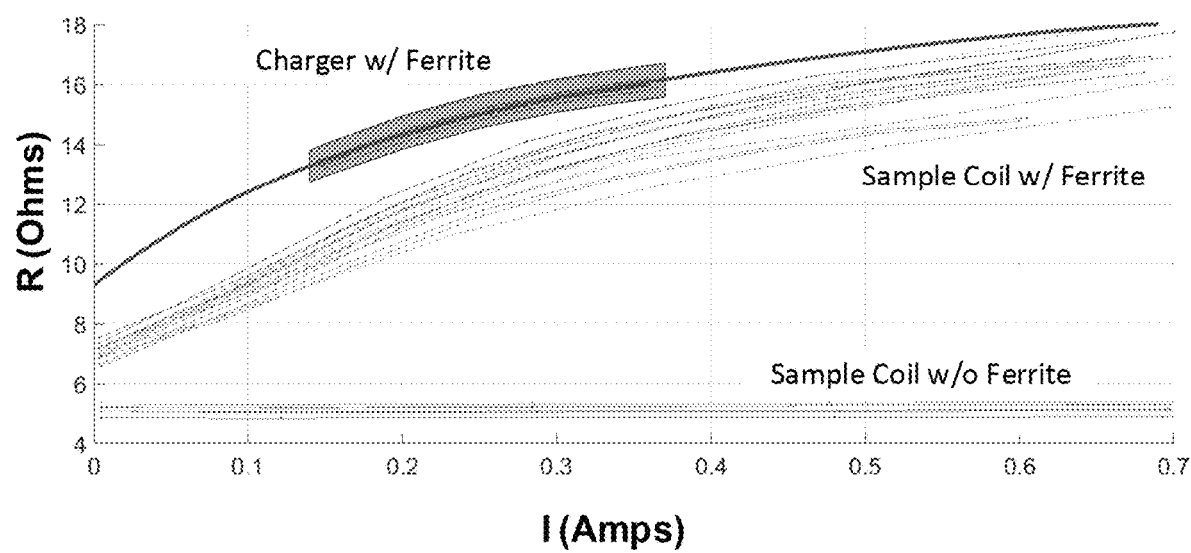
FIG. 5 is a graph of example resistance within the primary coil of an external charger as a function of recharge current for a 110 kHz recharge frequency examined within and without the inclusion of a ferrite material.

To confirm the influence of ferrite material 24 on the energy conservation of the system, additional experiments were conducted comparing the resistance of through sample primary coils as a function of frequency with and without the presence of a ferrite material positioned adjacent to the primary coil. FIG. 5 is a graph illustrating the example results observed for the correlation of the ferrite material adjacent to a primary coil (e.g., primary coil 23A). FIG. 5 includes the test results of a prototype charger with ferrite material 24 (e.g., charging device 22), a sample coil with a ferrite material adjacent to the coil, and a sample coil without ferrite material. As can be seen from FIG. 5 during a simulated recharge process, the presence of the ferrite material significantly affects the observed resistance within the primary coil. This effect is also exaggerated with increasing current being passed through the primary coil. This resistance increase and associated heat generated is even pronounced at relatively low recharge currents. The results shown in FIG. 5 were tested at about room temperature. It was also observed that increasing the temperature of the coil ($T_{PRIM}$) would cause a linear increase in resistance of about 0.008 Ω/° C. to about 0.12 Ω/° C. over the operating range of about 22° C.-40° C.

Without being bound by theory, the increased resistance $R_{PRIM}$ through primary coil 23A during the recharge process is believed to be due, in part, to the hysteresis effect induced by the presence of ferrite material 25. Hysteresis losses can arise in ferromagnetic materials as the energy required to polarize and depolarize magnetic domains within the material. In charging device 22, these losses typically occur only in ferrite material 24. Hysteretic losses occur in a changing magnetic field and increase with recharge frequency. This results from the ferrite's non-conductivity and operation well below its ferromagnetic resonance frequency (about 10 MHz). Hysteresis behavior of a material is set by the properties of the material such as the chemical composition, porosity, grain size, and the like. These microstructure properties are set during ferrite manufacture and may vary with process inputs such as base ferrite powder mixture, compaction force, sintering heat cycle, or other process steps. While the hysteresis losses can account for some of the characteristic increase of $R_{PRIM}$ with current, the hysteresis effect caused by ferrite material 24 cannot be the sole cause of the increased resistance because the increased resistance $R_{PRIM}$ through primary coil 23A is still observed even at very low currents where hysteresis losses become more negligible.

As the size of IMD 14 is reduced along with the size of rechargeable power source 18 and other components, the impedance of the electrodes or other battery circuitry may increase and cause resistive heat generated to increase. In addition, the reduction in size of IMD 14 may similarly require a reduction in the size of secondary coil 23B and a similar increase in the recharge frequency (and a decrease in wavelength) of the electromagnetic energy delivered by primary coil 23A to secondary coil 23B. This increase in frequency and circuitry, combined with the presence of ferrite material 24 make it particularly challenging to accurately assess the energy conservation during the recharge process in system 10. Therefore, in contrast with other recharge algorithms that use an energy conservation approach and assess the $R_{PRIM}$ as a fixed constant, for recharge systems 10 that include a ferrite material 24 as described, assessing $R_{PRIM}$ as a variable dependent on recharge frequency, primary coil 23A temperature, primary coil current ($I_{CHARGER}$), or a combination thereof provides a more accurate manner of assessing the heat generated of IMD 14 ($Q_{IMD}$) into the surrounding tissue of patient 12.

Based on the observed pattern of $R_{PRIM}$ within FIGS. 4 and 5, the $R_{PRIM}$ through primary coil 23A may be accurately estimated as a function of $I_{CHARGER}$ and the temperature of primary coil 23A ($T_{PRIM}$) for a selected recharge frequency using Equation (3):

$$R_{PRIM}=A_0+A_1*I_{CHARGER}+A_2*T_{PRIM} \qquad (3)$$

Where $A_0$, $A_1$, and $A_2$ represent constants empirically derived for a given recharge frequency, $I_{CHARGER}$ is the current passing through primary coil 23A during the recharge cycle, and $T_{PRIM}$ is the temperature in Celsius primary coil 23A measured by temperature sensor 59.

$A_0$, $A_1$, and $A_2$ may be determined by linear regression using empirical calibration data collected for a given device and $R_{PRIM}$, $I_{CHARGER}$, $T_{PRIM}$ values. $R_{PRIM}$, $I_{CHARGER}$ may be measured directly using a power analyzer, while $T_{PRIM}$ may be measured using sensor 59. While measuring these quantities during operation at a single known frequency, device 22 may be forced to operate across its full current and temperature range. $A_0$, $A_1$, and $A_2$ are selected by plotting current, resistance, and temperature, in x, y, z space and finding a best fit curve or plane. In such examples, the recharge frequency may be a set value depending on the external charging device 22 (e.g., set to the frequency the device will operate at). In all such examples, the determination of $A_0$, $A_1$, and $A_2$ and the calculation of $R_{PRIM}$ in Equation 3 may still be considered as a function of the recharge frequency, even though the recharge frequency may be set to a constant value during the recharge process.

While $R_{PRIM}$ in Equation 3 is assessed using a first order regression analysis, in other embodiments, $R_{PRIM}$ may also be determined using higher order regressions (for example involving $I_{CHARGER}^2$ terms or $I_{CHARGER}*T_{PRIM}$ in order to more accurately match empirical data for a given product). Higher order regressions may have had greater accuracy or precision in fitting the curve of FIG. 4, but may significantly increase the complexity and computational power needed to determine $R_{PRIM}$ during the recharge process. Further improvement in accuracy or precision of the regression analysis may be overshadowed by other factors that affect the recharge process during actual charging sessions (e.g., tissue properties of patient 12, alignment between coils, etc.). Thus, the potential improvements observable from a higher order regression analysis become negligible.

In some embodiments, the $A_0$, $A_1$, and $A_2$ may be empirically determined and set within the programming of external charger 22 as part of the initial system calibration process (e.g., prior to patient use). Such analysis may be conducted during product manufacturing and stored within memory 52 of external charger 22.

Based on the above determination of $R_{PRIM}$, and energy conservation Equations 1 and 2, system 10 may control the charging of rechargeable power source 18. For example, processing circuitry 50 of charging device 22 may use Equation 1 to estimate the heat generated $Q_{IMD}$ or temperature of IMD 14 during the recharge process to increase or decrease charge rates or charging durations to effectively limit temperatures of IMD 14 and the surrounding patient tissue adjacent to IMD 14 or external charging device 22. For example, processing circuitry 50 may monitor and compare the determined temperature or $Q_{IMD}$ to a threshold temperature or heat generated value stored in memory 52. The processing circuitry may then determine when the estimated temperature or heat generated by IMD 14 reaches the threshold value. When the determined temperature or heat generated meets or exceeds the threshold value (e.g., a $Q_{IMD}$ falling within or exceeding 100 mW to 600 mW or a IMD temperature falling within or exceeding 39° C. to 43° C.), the processing circuitry may control charging of rechargeable power source 18 by adjusting a power level used to charge rechargeable power source 18 by having, for example, processing circuitry 50 reduce the power level, turn the power off for a predetermined period of time (e.g., cycle the power on and off) or even terminate the charging session. For example, processing circuitry 50 may provide instructions to reduce the power used during the charging session, to cycle the power to control heat imparted to tissue (e.g., cycle it on and off), reduce the duty cycle of a charging waveform, or to terminate the charging session, in response to the determined heat generated or temperature for IMD 14 exceeding predetermined threshold values during the charging process. In other embodiments, the temperature(s) determined using the techniques described herein may be used to perform other or additional functions. For example, processing circuitry of the IMD or the external charging device may compare the determined temperature(s) to a fault condition threshold and disconnect the rechargeable power source from at least one electrical circuit when the determined temperature(s) exceed(s) the fault condition threshold, which may be performed during a time when a charging process is underway or during a time when a charging process is not underway.

In other embodiments, control of the charging process may be based on the estimated temperature of IMD 14 in conjunction with the cumulative thermal dose provided to the patient during the charging process. The cumulative thermal dose may be a metric used to quantify or estimate the total temperature exposure to tissue adjacent to IMD 14. As such, the cumulative thermal dose may be an estimated cumulative thermal dose. In one example, the cumulative thermal dose may be calculated by integrating the tissue temperature over a period of time. The resulting cumulative thermal dose may be used to equate the delivered heat to a certain tissue temperature level for a certain period of time. In one embodiment, it may be desirable to limit tissue exposure to heat for thirty minutes at forty-three degrees Celsius or less or to some other value that maintains patient comfort. Due to the variability in the temperature over the charging period, calculation of the cumulative thermal dose may allow a charging device or IMD 14 to determine when the desired limit to heat exposure is reached even if the actual tissue temperature varies over time. In other embodiments, the cumulative thermal dose may be calculated by adding the average temperature for multiple segments of the predetermined period of time. In any example, the cumulative thermal dose may be used to determine the total amount of heat or the extent of elevated temperature exposure for tissue surrounding or adjacent to IMD 14 during a recharging procedure being performed.

External charging device 22 may thus charge rechargeable power source 18 using one or more power levels or cycle times in some examples. In one example, external charging device 22 may select a "high" power level when first starting a charging session. External charging device 22 may then select a "low" power level, relative to the high-power level, in response to the estimated $Q_{IMD}$ or associated temperature reaching a threshold value. In this manner, the high-power level may charge rechargeable power source 18 at a high rate to reduce charging time while increasing the temperature of IMD 14. External charging device 22 may select the low power level to charge rechargeable power source 18 at a slower rate to reduce the temperature or rate of heat generation of IMD 14. A high-power level and a low power level may be subjective and relative to the charging power that external charging device 22 is capable of generating and transmitting to IMD 14.

In some embodiments, the high-power level may represent the maximum power level that external charging device 22 can generate. This high-power level also may be referred to as a boost, rapid, fast, or accelerated charging level because of the high rate of charge induced in rechargeable power source 18. By determining an accurate assessment of $Q_{IMD}$, $Q_{CHARGER}$, or both using Equations 1-3, the associate energy loss within system 10 may be accurately determined during the recharging session and external charging device 22 may charge rechargeable power source 18 with the high power level for a longer period of time without damaging tissue surrounding IMD 14.

In some embodiments, the high-power level may be approximately 2.5 Watts (W) and the power level may be approximately 1.0 W. However, other power levels and ranges may be selected for use, with such levels falling either within the above-described range or outside of this range depending on the particulars of the devices, arrangement of the recharge coils, or other factors. An example charge current level may be approximately 400 (mA) for the high-power level and approximately 100 mA for the low power level. An example primary coil 23A voltage and current for a high-power level may be approximately 4.5 V and approximately 800 mA and an example primary coil voltage and current for a low power level may be approximately 2.5 V and approximately 500 mA. These values are merely examples, and other examples may include higher, lower, or different values for these power levels for use in accordance with the techniques described herein. The recharge frequency may be about 1 kHz to about 1000 kHz, more preferably about 100 kHz to about 120 kHz.

Embodiments of the present disclosure may be used with a variety of implantable medical devices, including but not limited to nerve stimulation devices (also known as neuro stimulators or neuromodulation devices), drug delivery pumps, cardiac pacemakers, defibrillators, or implantable cardioverter-defibrillators. In embodiments, neuromodulation devices may be used to stimulate a variety of nerves or associated tissues for treating a variety of conditions. Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, sacral nerve stimulation, tibial nerve stimulation, gastric stimulation, and the like.

Figure 6:
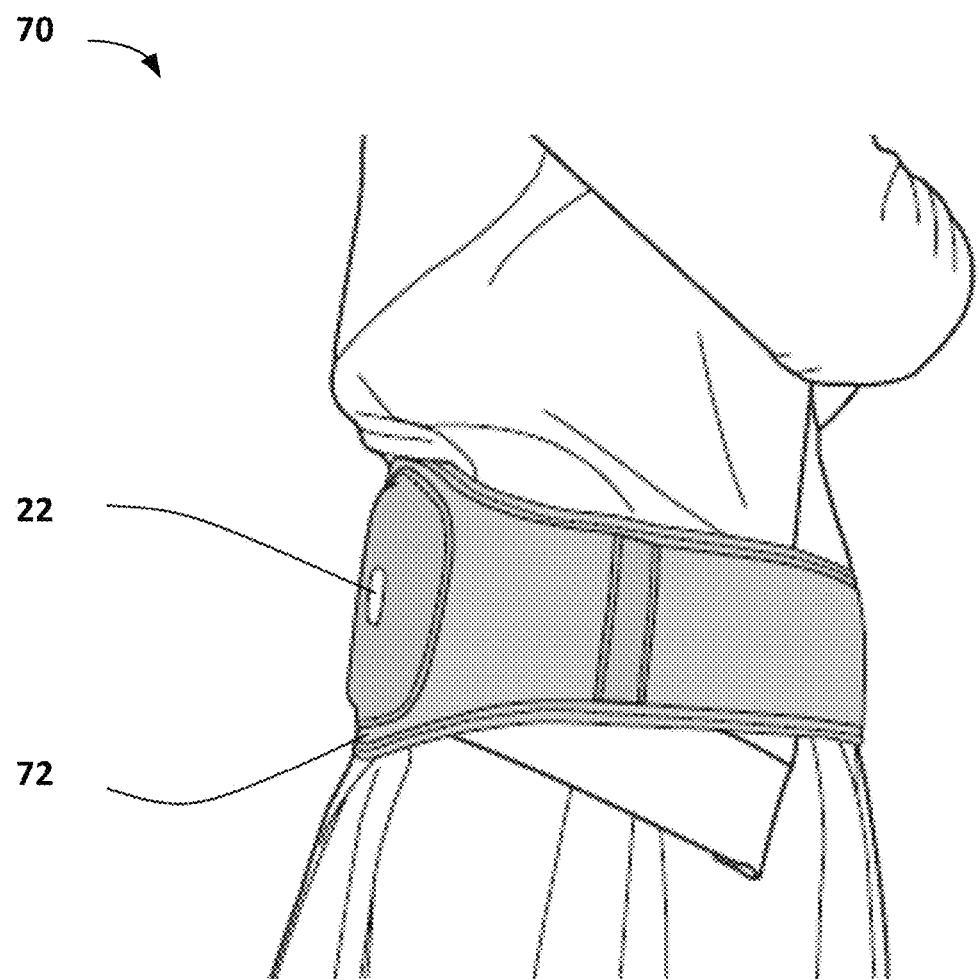
FIG. 6 is a conceptual diagram illustrating an example system that includes an IMD positioned along the lower back of a patient and the disclosed external charging device.

In an example, embodiments of the present disclosure may be used as part of a system for treating pelvic health conditions including incontinence, overactive bladder, pelvic pain or other pelvic floor disorders. Referring to FIG. 6, embodiments of the present disclosure can be implemented as part of a sacral nerve stimulation system 70, including a rechargeable IMD stimulation device (not shown) and external charging device 22, wherein external charging device 22 can be positioned on or proximate to skin of the patient over the location of the IMD to facilitate recharging. Referring to FIG. 6, external charging device 22 may also be wearable on the patient such as with a belt 72.

Figure 7:
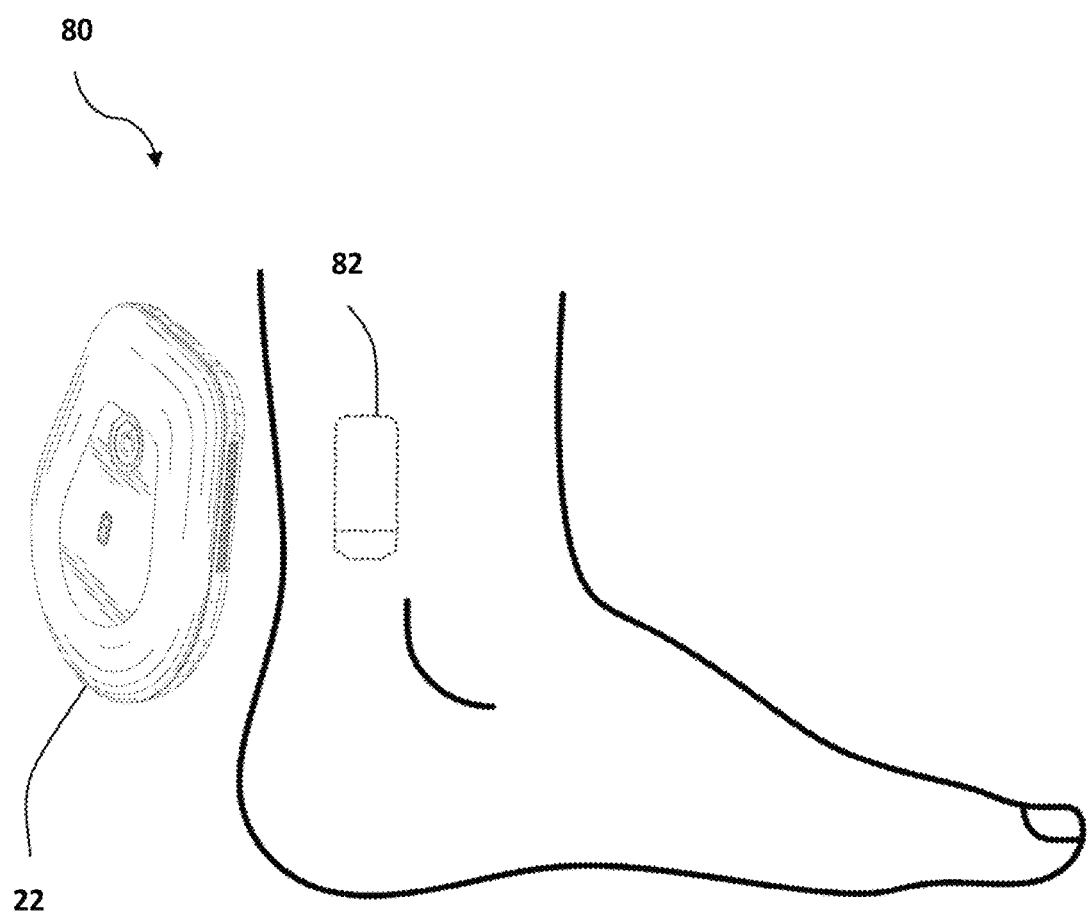
FIG. 7 is a conceptual diagram illustrating an example tibial nerve stimulation system that includes an IMD and the disclosed external charging device.

Referring to FIG. 7, in another example pertaining to treatment of pelvic health disorders, embodiments of the present disclosure may be implemented as part of a tibial nerve stimulation system 80, including IMD 82 in the form of a tibial nerve stimulation device and an external charging device 22, wherein external charging device 22 can be positioned on or proximate to skin of the patient over the location of IMD 82 to facilitate recharging. Tibial nerve stimulation system 80 may also include a wearable ankle cuff to hold external charging device 22 in position on an ankle of a patient.

Figure 8:
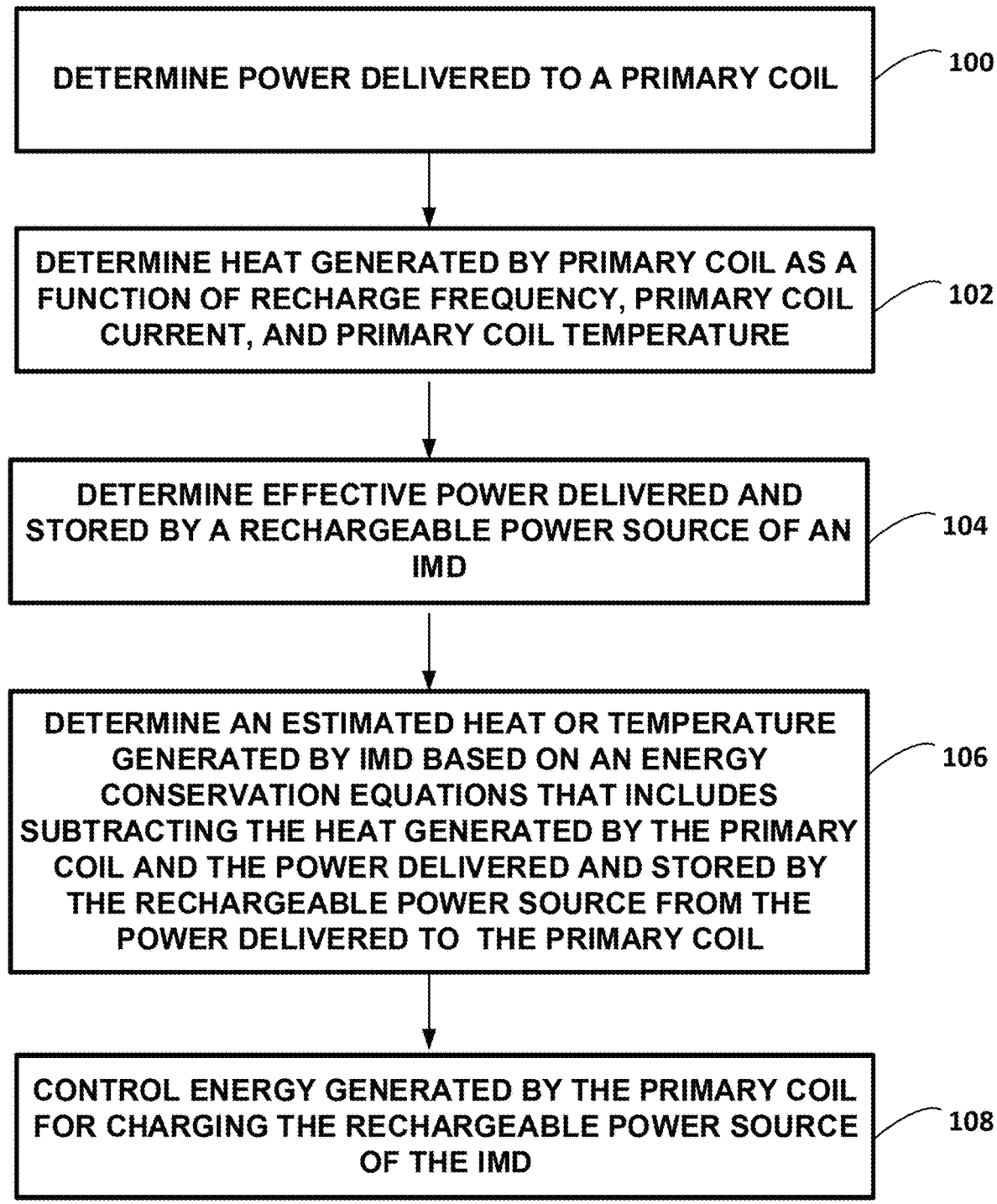
FIG. 8 is a flow diagram that illustrates an example technique for calculating an estimated energy loss within an IMD due to recharging and controlling energy generation by the external charging device based on the estimated energy transfer within the recharge system.

FIG. 8 is a flow diagram that illustrates an example technique for calculating an estimated heat generated by IMD 14 due to recharging and controlling energy generation by the external charging device based on the estimated heat generated by IMD 14. As shown in FIG. 8, during a charging session for rechargeable power source 18, processing circuitry 50 may determine a power ($P_{CHARGER}$) delivered to primary coil 23A (100). $P_{CHARGER}$ may be one or more set values or a continuous range of values. For example, $P_{CHARGER}$ may include a set of discrete power levels such as a low and high-power level for charging output. In other embodiments, $P_{CHARGER}$ may be a range of values that after an initial selection (e.g., startup charge at a high-power level) is continually adjusted and varied depending on the feedback from the energy conservation equation. In some embodiments, the $P_{CHARGER}$ may be set at an initial value of about 0.1 to 3.0 watts for the startup of the recharge session.

Processing circuitry 50 also determines the heat generated ($Q_{CHARGER}$) in the primary coil 23A as a function of recharge frequency, primary coil current ($I_{CHARGER}$), primary coil temperature ($T_{PRIM}$), or combinations thereof (102). As discussed above, heat generated in the primary coil ($Q_{CHARGER}$) may depend on variety of factors and system 10 design. In systems that include ferrite material 24 adjacent to primary coil 23A, the ferrite material can introduce a significant change in the resistance through primary coil 23A depending on the temperature of the coil, the recharge frequency used, the current passing through the primary coil 23A, as well as other factors. Processing circuitry 50 may determine the resistance through primary coil 23A ($R_{PRIM}$) as a function of temperature ($T_{PRIM}$) and coil current ($I_{CHARGER}$) based on Equation 3 for a given recharge frequency which is typically fixed at the time of manufacturing of external charger 22 (e.g., set at about 110 kHz). The constants $A_0$, $A_1$, and $A_2$ of Equation 3 may each be fixed and determined at the time of manufacturing/calibration of external charger 22 using one or more of the techniques described above. In other words, rather than assuming $R_{PRIM}$ is constant, processing circuitry 50 can monitor the selected recharge frequency, primary coil temperature, and primary coil current and make adjustments in the estimation of $R_{PRIM}$ during the recharge process. These adjustments to a given recharge process may be evaluated and made at set intervals (e.g., each microsecond, second, minute, etc.), at times when one or more of such variables are selectively altered, when system faults are detected (e.g., coils not coupling), or combinations thereof.

Using the estimated $R_{PRIM}$, the heat generated ($Q_{CHARGER}$) in the primary coil 23A may be determined according to Equation 2. As will be understood by those in the art, certain values need not be explicitly determined by processing circuitry 50 to determine the estimated heat generated in primary coil 23A in accordance with Equation 2. For example, $R_{PRIM}$ need not be explicitly calculated to determine $Q_{CHARGER}$. Instead, as an example, Equation 3 may be directly incorporated into Equation 2 to determine $Q_{CHARGER}$ without explicitly determining $R_{PRIM}$. It will be understood that such substitutions nevertheless determine $Q_{CHARGER}$ as a function of the recharge frequency, primary coil current, and primary coil temperature within the teaching of this disclosure.

Processing circuitry 50 also determines the effective power delivered to the rechargeable power source 18 ($P_{IMD}$) (104). $P_{IMD}$ may be determined using any suitable technique. In some embodiments $P_{IMD}$ may be determined by multiplying the charge current from second coil 23B and the voltage of rechargeable power source 18.

With the above determinations, processing circuitry 50 also determines an estimated heat generated ($Q_{IMD}$) or temperature of IMD 14 based on the energy conservation calculation (e.g., Equation 1) by subtracting the heat generated in primary coil 23A and the effective power transferred to rechargeable power source 18 from the power delivered to primary coil 23A (106). Depending on the design of system 10, the estimated $Q_{IMD}$ may be converted in to a temperature value or some other useful measure of the heat being generated by IMD 14 and released into the surrounding tissue of patient 12. Regardless of the value chosen, system 10 may include threshold parameters (e.g., threshold $Q_{IMD}$ value, temperature limit, duration limit for a set value, or the like) and processing circuitry 50 may monitor the recharge system 10 and reduce, increase, or cease recharger power or current ($P_{CHARGER}$ or $I_{CHARGER}$) to help maximize the recharging process during a given session while also maintaining system 10 within the threshold limits. For example, processing circuitry 50 may initiate an initial recharge session at a high-power setting. Processing circuitry 50 may then control energy generation by primary coil 23A for charging rechargeable power source 18 based on the estimated energy generated in IMD 14 (108) to maintain system 10 within a heat or temperature threshold. When the estimated $Q_{IMD}$ reaches a threshold limit, processing circuitry 50 may reduce the power or current supplied by the external charging device 22 or cease delivery of charge for a period of time, thereby reducing the total heat generated by IMD 14.

In contrast to a system that assumes a fixed $R_{PRIM}$, calculating $R_{PRIM}$ and therefore $Q_{CHARGER}$ as a function of the recharge frequency, primary coil current, and primary coil temperature provides a more accurate assessment of the heat generated and lost within system 10. The estimation of the heat generated by IMD 14 and transferred (e.g., lost) to the surrounding tissue may be more accurate and allow for system 10 to charge at a higher power setting for a longer period of time before reducing or ceasing the power delivered by external charging device 22.

In some embodiments, controlling the energy being generated by primary coil 23A may take into account the alignment between primary and secondary coils 23A and 23B and relative positions of IMD 14 and external charging device 22 when performing steps (100)-(108). For example, in situations where processing circuitry 50 has determined that the separation between primary and secondary coils 23A and 23B is relatively large (e.g., deep tissue placement of IMD 14), the coils are not optimally aligned, or both, the estimated heat ($Q_{IMD}$) or temperature generated by IMD 14 may remain relatively small during the entire recharge process due to the inefficient coil coupling. In some such scenarios, the recharge process may be controlled in a $Q_{CHARGER}$ limited setting to limit the amount of surface heat generated by the external charging device 22. The $P_{CHARGER}$ may be set to a high-power setting (e.g., about 1.5 W) and reduced when $Q_{CHARGER}$ begins to reach a threshold value. $Q_{IMD}$ may be monitored for safety but may not reach or near threshold limits during such recharge.

Alternatively, in situations where processing circuitry 50 has determined that the separation between primary and secondary coils 23A and 23B is relatively small (e.g., shallow tissue placement of IMD 14), the energy delivered to IMD 14 may be comparatively better and the estimated heat ($Q_{IMD}$) or temperature generated by IMD 14 may be the limiting factor in the recharge process. In some such scenarios, the recharge process may be controlled in a $Q_{IMD}$ limited setting to control the amount of heat generated by or the temperature reached by the IMD 14. The $P_{CHARGER}$ may be set to a lower power setting (e.g., about 0.6 W) and increased or decreased such that the system is controlled to maintain a relatively constant $Q_{IMD}$ near or below a threshold value.

Additionally, or alternatively, in situations where processing circuitry 50 has determined that the optimal coupling and energy transfer between primary and secondary coils 23A and 23B is present (e.g., shallow tissue placement of IMD 14 and perfect coil alignment) the energy delivered to IMD 14 may be limited by imposed circuitry limitations on the system, such as limited based on the current being delivered to rechargeable power source 18 to protect the integrity of power source 18 or other hardware. In such examples, the values of $Q_{IMD}$ and other parameters may still be monitored to ensure threshold values are not exceeded, but ultimately the heat generated in the system may not be the limiting factor. In all situations, one or more of the threshold limits discussed above may be set by the programmer, clinician, patient 12, or combinations thereof to provide both safety and comfort to patient 12 during the recharge process.

Steps (100)-(108), may be conducted in any order, independently one or more times, continually, or periodically throughout the recharge process. For example, step (102) of determining the heat generated by primary coil 23A may be periodically determined on an ongoing basis throughout a recharge cycle. The different charging scenarios described above may be switched between on an ongoing basis depending on the real-time feedback and charging information provided to processing circuitry 50.

In some embodiments, the energy conservation evaluation of system 10 may include one or more additional assessments of the energy lost during the recharge session. The additional factors may include, but are not limited to, estimating the energy absorbed by the surrounding tissue directly from the primary coil due to a specified absorption rate, energy lost due to coil misalignments, heat dissipation by the surrounding tissue, or the like. These additional considerations may help improve the precision and accuracy of the energy conservation analysis but are not necessary to for understanding the features or obtaining the benefits described herein.

Figure 9:
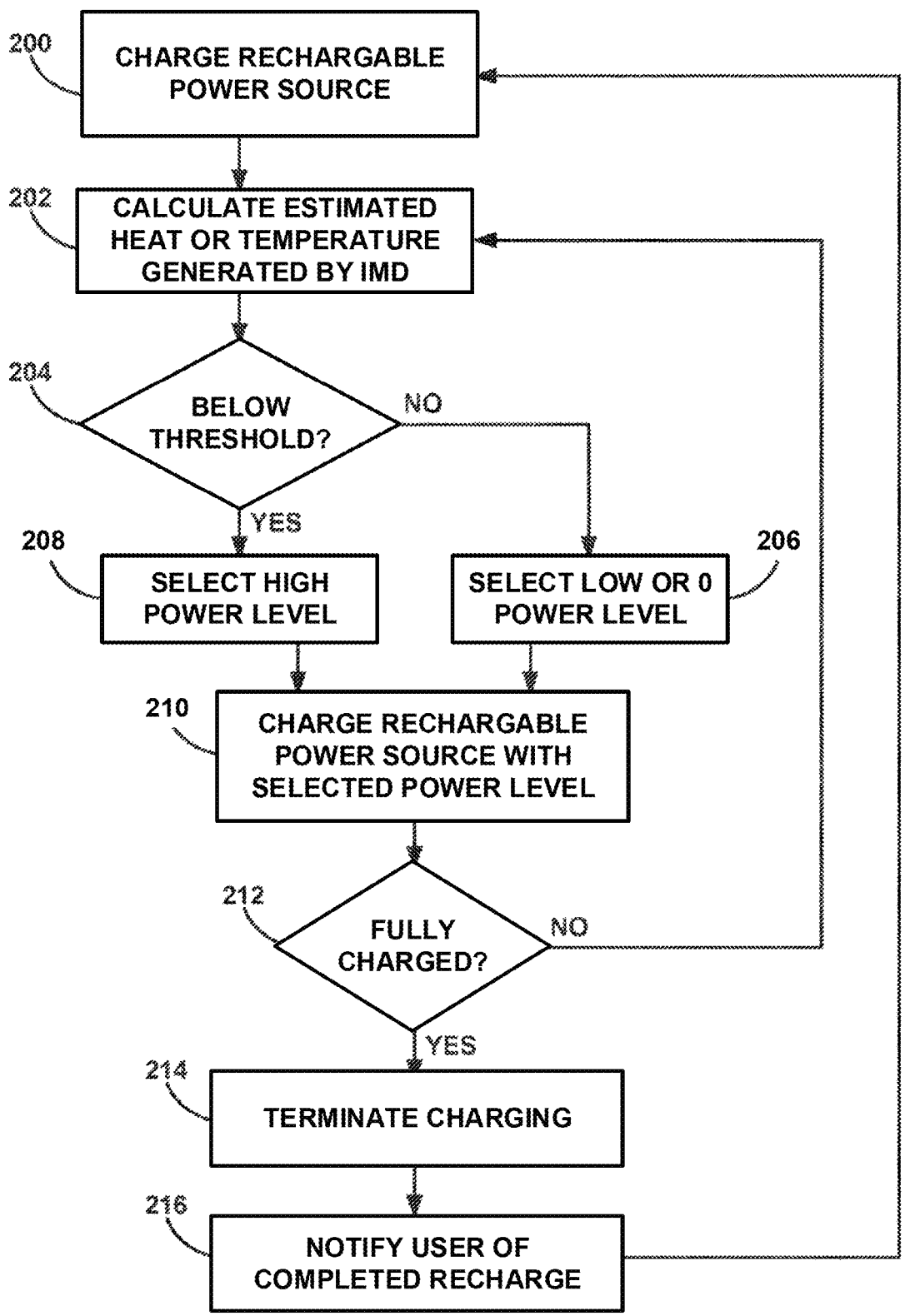
FIG. 9 is a flow diagram that illustrates an example technique for selecting a power level for charging an implantable rechargeable power source based on a calculated estimated energy transfer within the recharge system.

FIG. 9 is a flow diagram that illustrates an example technique for selecting a power level for charging an implantable rechargeable power source based on a calculated estimated energy transfer to tissue of patient 12. A charging session for rechargeable power source 18 may begin when processing circuitry 50 receives a charge request via user interface 54 (200). Processing circuitry 50 may calculate the estimated heat or temperature generated by IMD 14 (202). As described herein, in some examples, the estimated energy transfer may be calculated based on subtracting the heat generated of the primary coil ($Q_{CHARGER}$) and the effective power delivered to the battery from the power delivered to primary coil 23A ($P_{IMD}$) from the power being supplied by the primary coil ($P_{CHARGER}$). As described herein, the estimated energy transfer may be further calculated based on a variable primary coil 23A resistance ($R_{PRIM}$) that is adjusted based on the recharge frequency, current, and temperature.

The processing circuitry 50 may them determine if the estimated heat generated by IMD 14 or the estimated temperature of IMD 14 is below a set threshold value (204). If system 10 is operating below threshold limits, the "YES" branch of block 204 may be selected and processing circuitry 50 may set or maintain the recharge process at a high-power lever ($P_{CHARGER}$) (208) and charge rechargeable power source 18 at the high-power lever (210). If the estimated heat generated by IMD 14 or the estimated temperature of IMD 14 is near or above the set threshold value ("NO" branch of block 204), processing circuitry 50 selects either a low or zero power level for charging (210). If a zero-power level is selected, the system may wait a set period of time (e.g., a rest period) to allow components of system 10 to cool before reinitializing the charge. If processing circuitry 50 is switching from one charging power level to another, user interface 54 may notify the user via a sound or visual indication that such change has occurred. Processing circuitry 50 then instructs charging module 58 to charge with the selected power level (210).

If rechargeable power source 18 has not yet reached a 100 percent, or full, charge level ("NO" branch of block 212), then processing circuitry 50 continues to calculate the estimated heat generated by IMD 14 (202). If rechargeable power source 18 has reached a 100 percent, or full, charge level ("YES" branch of block 212), then processing circuitry 50 may instruct charging module 58 to terminate charging (214). In other words, processing circuitry 50 may select a zero-power level. Charging device 22 may subsequently notify the user of the completed recharge of rechargeable power source 18 and IMD 14 (216). This notification may be in the form of an audible alert or visual indicator provided by user interface 54. Processing circuitry 50 may also terminate charging upon request from the user.

In alternative examples, processing circuitry 50 may not charge rechargeable power source 18 when the estimated heat generated meets or exceeds a total heat threshold for a given recharge session. Therefore, not even a low power level would be selected. Although a low power level may be acceptable for charging at any time in some systems and patients, other systems may be programmed to not allow any charging after the heat generation threshold is exceeded.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

What is claimed is:

1. A method for controlling charging of a rechargeable power source of an implantable medical device (IMD) in a patient, the method comprising:
    determining, by processing circuitry of an external charging device, a power being delivered to a primary coil of the external charging device for recharging the IMD, wherein the external charging device comprises the primary coil and a ferrite material adjacent to the primary coil and spanning an aperture defined by the primary coil;
    determining, by the processing circuitry, an estimated power delivered to the rechargeable power source during charging of the IMD;
    calculating, by the processing circuitry, an estimated heat generated by the primary coil based on a resistance of the primary coil, wherein the resistance of the primary coil is determined as a function of at least one of a recharge frequency, a temperature of the primary coil, and a current supplied to the primary coil, the resistance of the primary coil determined as a variable so as to account for the presence of the ferrite material in the external charging device;
    calculating, by the processing circuitry, an estimated heat generated by the IMD by subtracting the estimated heat generated by the primary coil and the estimated power delivered stored by the rechargeable power source from the power being delivered to a primary coil; and
    controlling, by the processing circuitry and based on the heat generated by the IMD, the power being delivered by the primary coil of the external charging device, wherein the estimated heat generated by the primary coil is determined at least in part by empirically derived values for a given recharge frequency based on a regression analysis fitting a curve to a measured coil resistance for the primary coil as a function of frequency for a given temperature of the primary coil.

2. The method of claim 1, wherein the estimated heat generated by the primary coil is determined based on below Equation 2:

$$Q_{CHARGER} = R_{PRIM} * (I_{CHARGER})^2 \quad (2)$$

wherein $Q_{CHARGER}$ is the estimated heat generated by the primary coil; $R_{PRIM}$ is the resistance through a recharge circuit including the primary coil; and $I_{CHARGER}$ is the current passed through the primary coil.

3. The method of claim 2, wherein $R_{PRIM}$ is variable dependent on the recharge frequency, the temperature of the primary coil ($T_{PRIM}$), and $I_{CHARGER}$.

4. The method of claim 3, wherein $R_{PRIM}$ is calculated based on below Equation (3):

$$R_{PRIM} = A_0 + A_1 * I_{CHARGER} + A_2 * T_{PRIM} \quad (3)$$

wherein $T_{PRIM}$ is a temperature of the primary coil; and $A_0$, $A_1$, and $A_2$ are empirically derived values for a given recharge frequency based on a regression analysis fitting a curve to a measured coil resistance for the primary coil as a function of frequency for a given $T_{PRIM}$.

5. The method of claim 1, wherein the IMD does not include a temperature sensor.

6. The method of claim 1, wherein the resistance of the primary coil is determined as a function the recharge frequency, the temperature of the primary coil, and the current supplied to the primary coil.

7. The method of claim 1, wherein the external charger is configured to deliver recharge power at a recharge frequency of greater than 40 kHz.

8. The method of claim 1, wherein the external charger is configured to deliver recharge power at a recharge frequency of about 100 kHz and 120 kHz.

9. The method of claim 1, wherein controlling the power being delivered by the primary coil of the external charging device comprises:
    calculating, by the processing circuitry, the estimated heat generated by the IMD reaches or exceeds a predetermined threshold, reducing or ceasing the power being delivered to a primary coil.

10. An external charging device comprising:
    a primary coil configured to provide recharge power to a rechargeable power source of an implantable medical device (IMD) through transcutaneous charging;
    a ferrite material adjacent to the primary coil and spanning an aperture defined by the primary coil; and
    processing circuitry configured to:
        determine a power being delivered to the primary coil of the external charging device for recharging the IMD;
        determine an estimated power delivered stored by the rechargeable power source during charging of the IMD;
        calculate an estimated heat generated by the primary coil based on a resistance of the primary coil, wherein the resistance of the primary coil is determined as a function of at least one of a recharge frequency, a temperature of the primary coil, and a current supplied to the primary coil, the resistance of the primary coil determined as a variable to account for the presence of the ferrite material in the external charging device;

calculate an estimated heat generated by the IMD by subtracting the estimated heat generated by the primary coil and the estimated power delivered stored by the rechargeable power source from the power being delivered to the primary coil; and control, based on the heat generated by the IMD, the power being delivered by the primary coil of the external charging device, wherein the estimated heat generated by the primary coil is determined at least in part by empirically derived values for a given recharge frequency based on a regression analysis fitting a curve to a measured coil resistance for the primary coil as a function of frequency for a given temperature of the primary coil.

11. The external charging device of claim 10, wherein the estimated heat generated by the primary coil is determined based on below Equation 2:

$$Q_{CHARGER} = R_{PRIM} * (I_{CHARGER})^2 \qquad (2)$$

wherein $Q_{CHARGER}$ is the estimated heat generated by the primary coil; $R_{PRIM}$ is the resistance through a recharge circuit including the primary coil; and $I_{CHARGER}$ is the current passed through the primary coil.

12. The external charging device of claim 11, wherein $R_{PRIM}$ is variable dependent on the recharge frequency, the temperature of the primary coil, and $I_{CHARGER}$.

13. The external charging device of claim 12, wherein $R_{PRIM}$ is calculated based on below Equation (3):

$$R_{PRIM} = A_0 + A_1 * I_{CHARGER} + A_2 * T_{PRIM} \qquad (3)$$

wherein $T_{PRIM}$ is a temperature of the primary coil; and $A_0$, $A_1$, and $A_2$ are empirically derived values for a given recharge frequency based on a regression analysis fitting a curve to a measured coil resistance for the primary coil as a function of frequency for a given $T_{PRIM}$.

14. The external charging device of claim 10, wherein the processing circuitry does not rely on a measured temperature of the IMD to calculate the estimated heat generated by the IMD.

15. The external charging device of claim 10, wherein the external charging device is configured to deliver recharge power at a recharge frequency of greater than 40 kHz.

16. The external charging device of claim 10, wherein the external charging device is configured to deliver recharge power at a recharge frequency about 100 kHz and about 120 kHz.

17. The external charging device of claim 10, wherein to control the power being delivered by the primary coil of the external charging device, the processing circuitry calculates the estimated heat generated by the IMD reaches or exceeds a predetermined threshold and then reduces or ceases the power being delivered to a primary coil.

18. A system comprising:
an implantable neurostimulator device comprising a housing containing a rechargeable power source; and
an external charging device comprising:
a primary coil configured to provide recharge power to the rechargeable power source of the implantable neurostimulator device through transcutaneous charging;
a ferrite material adjacent to the primary coil and spanning an aperture defined by the primary coil; and
processing circuitry configured to:
determine a power being delivered to the primary coil of the external charging device for recharging the implantable neurostimulator device;
determine an estimated power delivered stored by the rechargeable power source during charging of the implantable neurostimulator device;
calculate an estimated heat generated by the primary coil based on a resistance of the primary coil, wherein the resistance of the primary coil is determined as a function of at least one of a recharge frequency, a temperature of the primary coil, and a current supplied to the primary coil, the resistance of the primary coil determined as a variable to account for the presence of the ferrite material in the external charging device;
calculate an estimated heat generated by the implantable neurostimulator device by subtracting the estimated heat generated by the primary coil and the estimated power delivered stored by the rechargeable power source from the power being delivered to the primary coil; and
control, based on the heat generated by the implantable neurostimulator device, the power being delivered by the primary coil of the external charging device,
wherein the estimated heat generated by the primary coil is determined at least in part by empirically derived values for a given recharge frequency based on a regression analysis fitting a curve to a measured coil resistance for the primary coil as a function of frequency for a given temperature of the primary coil.

19. The system of claim 18, wherein the estimated heat generated by the primary coil is determined based on below Equation 2:

$$Q_{CHARGER} = R_{PRIM} * (I_{CHARGER})^2 \qquad (2)$$

wherein $Q_{CHARGER}$ is the estimated heat generated by the primary coil; $R_{PRIM}$ is the resistance through a recharge circuit including the primary coil; and $I_{CHARGER}$ is the current passed through the primary coil.

20. The system of claim 19, wherein $R_{PRIM}$ is variable dependent on the recharge frequency, the temperature of the primary coil, and $I_{CHARGER}$.

* * * * *

UNITED STATES PATENT AND TRADEMARK OFFICE
CERTIFICATE OF CORRECTION

PATENT NO.         : 11,896,838 B2
APPLICATION NO.    : 17/078479
DATED              : February 13, 2024
INVENTOR(S)        : Fried et al.

It is certified that error appears in the above-identified patent and that said Letters Patent is hereby corrected as shown below:

In the Claims

Column 22, Line 20, please delete:
"$R_{PRIM} - A_0 + A_1*I_{CHARGER} + A_2*T_{PRIM}$     (3)"
And replace with:
$R_{PRIM} = A_0 + A_1*I_{CHARGER} + A_2*T_{PRIM}$     (3)

Signed and Sealed this
Twenty-fifth Day of February, 2025

Coke Morgan Stewart
*Acting Director of the United States Patent and Trademark Office*